United States Patent [19]

Min et al.

[11] Patent Number: 5,713,924
[45] Date of Patent: Feb. 3, 1998

[54] DEFIBRILLATION THRESHOLD REDUCTION SYSTEM

[75] Inventors: Xiaoyi Min, Plymouth; Luc R. Mongeon; Michael R. S. Hill, both of Minneapolis, all of Minn.

[73] Assignee: Medtronic, Inc., Minneapolis, Minn.

[21] Appl. No.: 495,251

[22] Filed: Jun. 27, 1995

[51] Int. Cl.$^6$ ........................................................ A61N 1/39
[52] U.S. Cl. ........................................................ 607/4
[58] Field of Search ........................................ 607/4, 5, 14

[56] References Cited

U.S. PATENT DOCUMENTS

| | | |
|---|---|---|
| 3,937,226 | 2/1976 | Funke . |
| 4,222,386 | 9/1980 | Smolnikov . |
| 4,275,737 | 6/1981 | Thompson . |
| 4,340,062 | 7/1982 | Thompson . |
| 4,406,286 | 9/1983 | Stein . |
| 4,407,288 | 10/1983 | Langer . |
| 4,548,209 | 10/1985 | Wielders . |
| 4,595,009 | 6/1986 | Leinders . |
| 4,649,931 | 3/1987 | Beck . |
| 4,693,253 | 9/1987 | Adams . |
| 4,726,380 | 2/1988 | Vollmann . |
| 4,726,383 | 2/1988 | Cook . |
| 4,727,877 | 3/1988 | Kallok . |
| 4,787,389 | 11/1988 | Tarjan ............................ 607/4 |
| 4,830,006 | 5/1989 | Haluska . |
| 4,880,005 | 11/1989 | Pless . |
| 4,958,632 | 9/1990 | Duggan . |
| 4,969,463 | 11/1990 | Dahl . |
| 5,022,395 | 6/1991 | Russie . |
| 5,074,301 | 12/1991 | Gill . |
| 5,161,528 | 11/1992 | Sweeney . |
| 5,163,427 | 11/1992 | Keimel . |
| 5,165,403 | 11/1992 | Mehra . |
| 5,174,288 | 12/1992 | Bardy . |
| 5,184,616 | 2/1993 | Weiss . |
| 5,193,536 | 3/1993 | Mehra . |
| 5,314,448 | 5/1994 | Kroll . |
| 5,318,591 | 6/1994 | Causey . |
| 5,366,485 | 11/1994 | Kroll . |
| 5,458,619 | 10/1995 | Olson ............................ 607/4 |
| 5,464,429 | 11/1995 | Hedberg et al. ............... 607/4 |
| 5,500,004 | 3/1996 | Ansourian et al. ............ 607/4 |
| 5,562,708 | 10/1996 | Combs et al. ................. 607/4 |

FOREIGN PATENT DOCUMENTS

| | | | |
|---|---|---|---|
| 0588125 | 3/1994 | European Pat. Off. | ........ A61N 1/365 |
| 0599588 | 6/1994 | European Pat. Off. | .......... A61N 1/39 |
| 9218198 | 10/1992 | WIPO . | |
| 9528988 | 11/1995 | WIPO | ................ A61N 1/39 |

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

A method an apparatus for treating fibrillation, particularly atrial fibrillation. In response to detection of fibrillation, a high frequency, low energy pulse burst is delivered via pacing electrodes, accompanied by a high energy pulse delivered via defibrillation electrodes. The low energy pulse burst is preferably delivered to an area of the heart which exhibits relatively lower current density during delivery of the high energy pulse.

34 Claims, 3 Drawing Sheets

DEFIBRILLATION THRESHOLD REDUCTION SYSTEM

CROSS-REFERENCE TO RELATED APPLICATION

Reference is hereby made to commonly assigned, copending U.S. patent application Ser. No. 08/230,578, filed by Mongeon et al on Apr. 24, 1994 for a "Method and Apparatus for Treatment of Atrial Fibrillation", now abandoned.

FIELD OF THE INVENTION

The present invention generally relates to an implantable device for applying defibrillating electrical energy or shock to at least one chamber of a patient's heart in need of defibrillation, and to a method and apparatus for reducing the threshold energy required to effect the defibrillation and, in the case of atrial defibrillation, to thereby reduce the pain attendant to the delivery of the defibrillation energy.

BACKGROUND OF THE INVENTION

Fibrillation has generally been treated by means of high energy cardioversion/defibrillation shocks or pulses, which, in the context of implantable anti-arrhythmia devices, are applied by means of large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

Over the years, numerous methods have been proposed for pacing or synchronously cardioverting a heart chamber in an attempt to interrupt tachycardias other than fibrillation. The pacing therapies include such pacing modalities as overdrive pacing, burst pacing, autodecremental overdrive pacing, and others, and synchronization with the underlying heart depolarizations may or may not be included. These pacing modalities have been formulated to interrupt aberrant reentrant conduction which may lead to sustained tachycardias in one or more chambers of the heart.

It has also been proposed that tachycardias could be prevented or interrupted by the use of simultaneous or timed multi-site cardiac pacing. One early example of multi-site cardiac pacing to terminate or prevent tachyarrhythmia is disclosed in U.S. Pat. No. 3,937,226 issued to Funke. In this device, a number of small surface area pacing electrodes are provided, each coupled to a separate output circuit and amplifier. The disclosed device is equivalent to five or more separate cardiac pacemaker output circuits of conventional design, all adapted to be triggered to pace simultaneously at various locations around the heart. It is hypothesized that by stimulating simultaneously at locations spread around the heart, synchronous with a sensed QRS complex, arrhythmias could be prevented by producing a more nearly simultaneous depolarization of cardiac tissues.

These approaches have been proposed and tested in the hope that the low energy pacing pulses would terminate the tachyarrythmia without having to resort to higher energy cardioversion therapies. This has been particularly of interest for treating frequently recurring tachyarrhythmias, since the battery life of the stimulation device depends on the amount of energy expended in delivering a therapy and the delivery frequency.

In the case of atrial fibrillation, the patient is not rendered unconscious if the ventricles continue to provide adequate cardiac output. Unfortunately, the quantity of electrical energy which is required to defibrillate the atria is sufficient, in most cases, to cause a sudden, propagated pain in the patient's chest area or to stun the patient. Typically reported defibrillation thresholds between transvenous leads bearing electrodes placed in the right atrium and/or superior vena cava (RA/SVC) and in the coronary sinus (CS) often exceed 2 J. Significant discomfort and or extreme pain can be associated with transvenous shock therapy in this range, resulting in sedation of some patients and refusal to accept the therapy by other patients.

Use of pacing energy pulses delivered at multiple sites within the atria to prevent the occurrence of atrial tachyarrhythmias including atrial flutter, which may in some cases progress to atrial fibrillation, has been investigated. For example, the article "Prevention of Atrial Tachyarrhythmias Related to Advanced Interatrial Block by Permanent Atrial Resynchronization", by Daubert et al, *PACE*, Vol.14, P. 648, 1991, discloses the use of synchronized pacing pulses delivered to the right and left atria to prevent onset of atrial tachyarrhythmias.

Recently, the theoretical possibility of employing low energy pacing level pulses (i.e. less than 0.05 joules) to treat atrial fibrillation has been explored. For example, in the recent article "Regional Control of Atrial Fibrillation by Rapid Pacing in Conscious Dogs", by Allessie et al, published in *Circulation*, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site has been demonstrated. However, the depolarization wavefront created by such pulses does not propagate through the entire chamber, due to the varying polarization states of the tissue surrounding the stimulation site. In the above cited application by Mongeon et al, delivery of high frequency, unsynchronized low energy pulse bursts to one or more sites in the heart is proposed as a treatment for atrial fibrillation.

Delivery of pulse bursts to the atrium in the presence of atrial fibrillation is also disclosed in U.S. patent application Ser. No. 08/082,327, for a "Method and Apparatus for Treatment of Atrial Fibrillation and Flutter", filed Jun. 24, 1993 by Bardy et al. In this device, pulse bursts are delivered in response to detected high ventricular rate, in patients having persistent or frequent atrial fibrillation. The pulse bursts are synchronized to individual heart depolarizations and are intended to stimulate the nerves within the AV nodal fat pad, to produce partial heart block and thus reduce ventricular rate, if it is tracking the high atrial rate.

Delivery of high frequency pulse bursts to the atrium is also known to induce atrial fibrillation, unless synchronized to atrial depolarizations or P waves to assure that the pulse bursts occur within the refractory period of the atrium. This effect is discussed in U.S. patent application Ser. No. 08/086,278, for a "Method and Apparatus for Treatment of Angina", filed Jun. 30, 1993, by Bardy, which discloses a device which provides pulse bursts to the atrium, synchronized to detected atrial depolarizations, to stimulate the SA nodal fat pad and reduce the sinus rate of patients who suffer from angina.

Synchronization to a high atrial or ventricular depolarization rate may be difficult to accomplish. In commonly assigned U.S. Pat. No. 5,193,536 to Mehra, a pacemaker/cardioverter/defibrillator is described where the high atrial or ventricular rate is made more regular by delivering overdrive pacing pulses into a tachycardia, which are intended to individually capture or pace the entire heart chamber (not believed possible in the case of fibrillation) and by using the last overdrive pacing pulse delivered as a synchronization event to time the delivery of a cardioversion pulse. Another method of employing pacing pulses as an aid to synchronization of cardioversion pulses is disclosed in U.S. Pat. No. 5,074,301 to Gill where a single pacing pulse is delivered to the atrium to allow a ventricular cardioversion pulse to be delivered in the atrial refractory period.

In U.S. Pat. No. 5,318,591 issued to Causey et al., charging of the high voltage capacitors during antitachycardia pacing is disclosed, to allow prompt delivery of a cardioversion pulse in the event the antitachycardia pacing pulses are unsuccessful in terminating a detected tachycardia. In U.S. patent application Ser. No. 08/159,351, filed Nov. 29, 1993 by Olson for an "Apparatus and Method for Treating a Tachyarrhythmia", a similar device is disclosed. Both the Olson and Causey devices treat antitachycardia pacing and high voltage shock as separate therapies and thus require a period of time following termination of the antitachycardia pacing pulses to check whether the pacing pulses were effective in terminating the tachyarrhythmia, and precondition the delivery of the high voltage shock on failure to terminate.

In U.S. Pat. Nos. 5,314,448 and 5,366,485 to Kroll et al., a cardioverter/defibrillator is described having a set of defibrillation electrodes arranged around the patient's heart. When fibrillation is detected, the high output capacitors begin to be charged. As they are charged or after full charge is achieved, a "pretreatment" of the fibrillating heart muscle is commenced through the generation of a train of pulses from the voltage on the output capacitors and delivery of the pulses across the defibrillation electrodes. The capacitors are recharged and at the end of the recharge time period, the high energy defibrillation pulse is delivered across the defibrillation electrodes. It is stated that the pretreatment pulses begin the process of organizing the chaotically contracting myocardial cells and result in a reduction of cardioversion threshold and the total energy expended. It is emphasized that the pretreatment pulse voltages are well in excess of pacing level voltages and that the same cardioversion electrodes are employed to deliver the energy to the same myocardial cells as will be defibrillated by the cardioversion pulse.

Despite these advances, a need continues to exist for atrial and ventricular cardioversion systems that can defibrillator the atria or ventricles at low energy to decrease energy consumption and pain perceived by the patient.

SUMMARY OF THE INVENTION

It is therefore an object of the present invention to provide an atrial or ventricular defibrillation method and apparatus that operates to defibrillate the atria or ventricles with lower energy pulses than otherwise would be required.

The present invention is directed toward providing a method and apparatus for reducing the defibrillation threshold by using a combined therapy including a burst of pacing energy, high frequency pulses applied into a low current density region of the cardiac tissue in the chamber in fibrillation in conjunction with the delivery of defibrillation pulses. It is not intended that the pulse burst itself terminate the detected fibrillation, and no attempt is made to determine whether the pulse burst has affected the heart rhythm as a precondition to high energy shock delivery. The burst of pacing energy pulses is delivered to a pacing electrode or electrodes located within the heart chamber in fibrillation, in an area which exhibits a relatively lower current density during application of a defibrillation pulse. The burst of pacing energy pulses injected into the low current density region is believed to result in an area of refractory, depolarized tissue and/or an increased opportunity of depolarization wavefront collisions in the vicinity of the pacing electrode or electrodes with the result that the defibrillation threshold for the following defibrillation pulse is lowered. The delivery of the pulse burst may also prevent ectopic beats originating in the low energy region from re-fibrillating the heart, after delivery of the defibrillation pulse.

While it is believed that the invention may be of benefit in reducing ventricular cardioversion energy thresholds, the invention is believed primarily valuable in the context of treating atrial fibrillation, as reducing the energy of the defibrillation shocks or pulses delivered to the atrium reduces both the associated level of pain and reduces the possibility that such shocks could trigger ventricular tachycardia or fibrillation.

The present invention surprisingly addresses these objectives by applying a pulse burst to the heart chamber of a type known to induce fibrillation, in conjunction with delivery of a defibrillation pulse. The pulse burst comprises a series of low energy pulses, typically less than about 10.0 volts, preferably of about 5.0 volts or less. The pulse frequency is preferably greater than 20 Hz, typically in the range of about 50–200 Hz. The burst is typically asynchronous to sensed heart depolarizations in the fibrillating heart chamber, and delivery may be commenced during the charge up of the high voltage, cardioversion energy, capacitors. The burst duration may be on the order of 1 to 5 seconds, with pulse bursts in the vicinity of 1 second preferred in the atrium. The burst may continue during the delivery of the defibrillation pulse and terminate just prior to the end of delivery of the defibrillation pulse. Alternatively, the burst may be terminated immediately prior to or a short interval prior to delivery of the defibrillation pulse to the defibrillation electrodes.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The timed delivery of pacing energy pulse bursts to pace/sense electrodes in the heart chamber to be defibrillated in relation to the subsequent delivery of a defibrillation shock or pulse to defibrillation electrodes for the same heart chamber may be implemented in a modified single chamber or dual pacemaker/cardioverter/defibrillator with any of the known pacing and defibrillation lead/electrode systems for single or dual chamber use. The invention may be practiced in a single chamber embodiment using separate pace/sense and defibrillation electrodes. However, the preferred use of the invention in lowering atrial defibrillation thresholds to reduce pain to the patient and to prolong battery life may be practiced in an embodiment using separate atrial pace/sense and defibrillation electrodes, along with a set of ventricular sense electrodes (and a ventricular sense amplifier and processing circuit) for detecting ventricular heart depolarizations so that the atrial defibrillation pulse is timed to fall outside the vulnerable period of the ventricle to lessen the risk of provoking ventricular fibrillation. In this case, due to the possibility of inducing ventricular fibrillation, the device may take the form of a pacemaker/cardioverter/defibrillator of the type depicted in FIG. 1, which also includes ventricular defibrillation capabilities, to provide an extra margin of safety. In such a comprehensive, dual chamber, pacemaker-cardioverter-defibrillator system embodiment of the invention, any of various embodiments of the invention may also be practiced by suitable programming of the specific operations performed by the system components.

Figure 1:
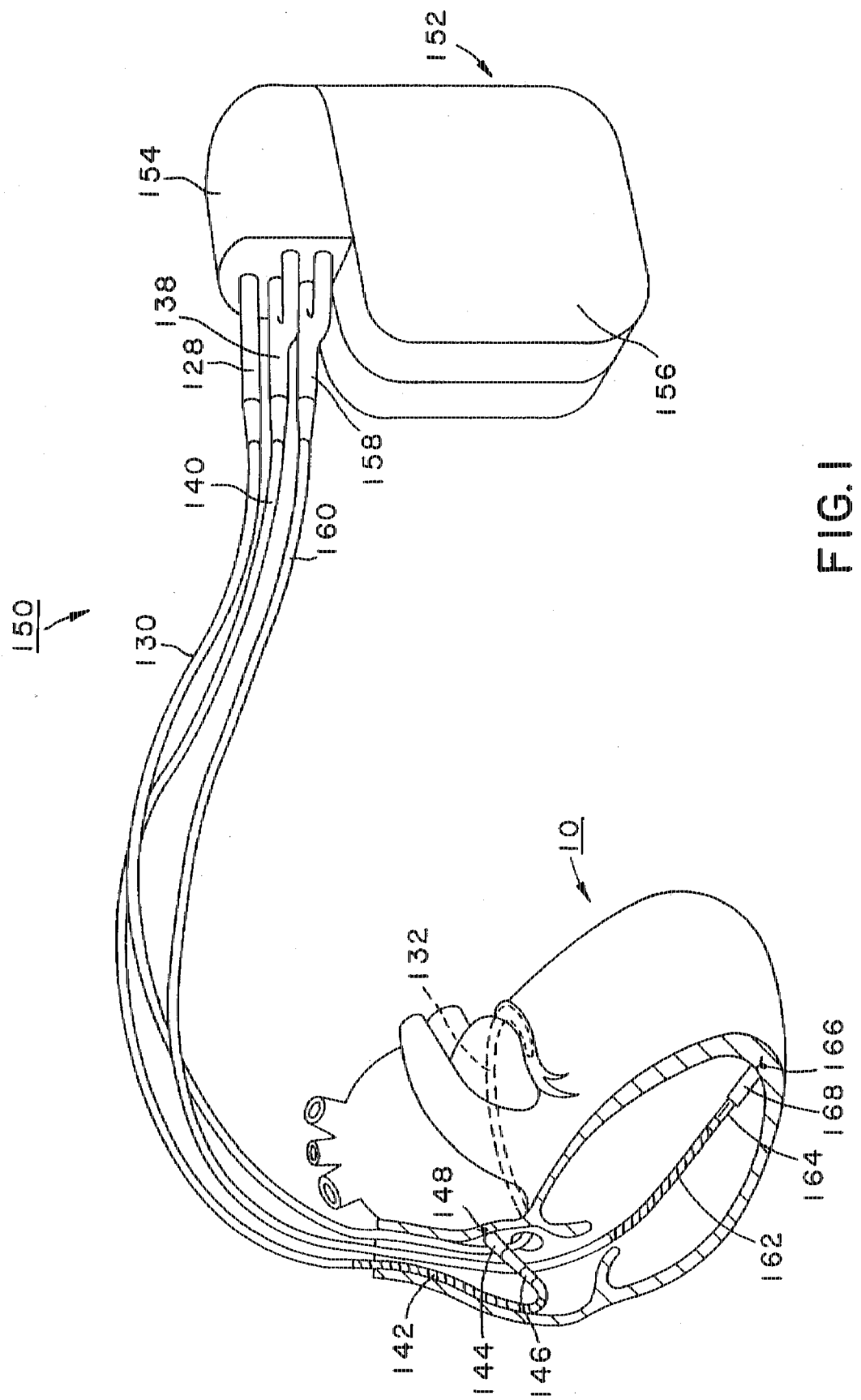
FIG. 1 is a plan view of an implantable pacemaker/cardioverter/defibrillator of the type in which the present invention may be embodied including a set of cardioversion and pace/sense leads illustrating exemplary locations of the defibrillation and pace/sense electrodes in relation to a human heart.
Figure 2:
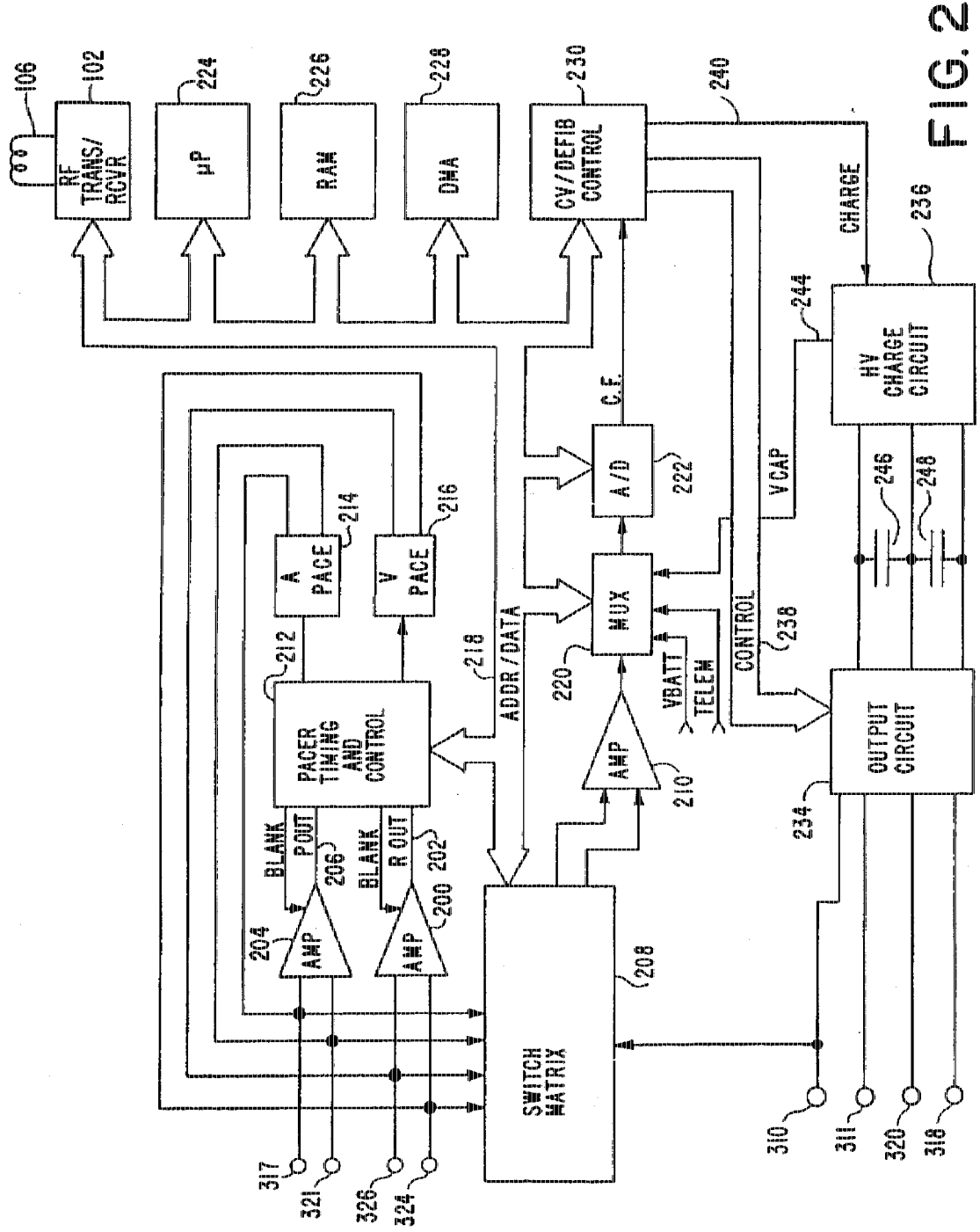
FIG. 2 is a comprehensive block diagram of a dual chamber, implantable pacemaker/cardioverter/defibrillator pulse generator of the type in which the present invention may be embodied.

FIGS. 1 and 2 therefore illustrate a comprehensive dual chamber system which is illustrative of all disclosed embodiments of the invention. FIG. 1 schematically illustrates such a pacemaker/cardioverter/defibrillator system 150, including a pulse generator 152 and a lead set, including a CS lead 130, an RA/SVC lead 140, and a ventricular or RV lead 160. The RV lead 160 may take the form of the ventricular leads disclosed in the above cited patents issued to Bardy, and includes three coaxial, coiled wire conductors separated from one another by tubular insulating sheaths. A ring electrode 164 and an extendable helix tip electrode 166, mounted retractable within an insulating electrode head 168, are located adjacent the distal end of the lead 160 and form a ventricular pace/sense, bipolar electrode pair. An elongated, exposed coil, defibrillation electrode 162 is located proximally to electrode head 168 and within the right ventricle. The RV defibrillation electrode 162 may be fabricated from platinum, platinum alloy or other materials known to be usable in implantable defibrillation electrodes and may be about 5 cm in length. Pace/sense electrodes 164 and 166 are employed for ventricular cardiac pacing and for sensing ventricular depolarizations or R-waves in a manner well known in the art. Each of the electrodes 162, 164, and 166 is coupled to one of the coiled conductors within the RV lead 160 which are coupled to three respective electrical connectors in a proximal end, bifurcated connector 158 which is in turn attached to receptacles in a connector block 154.

The RA/SVC lead 140 is constructed in a similar manner and includes a J-shaped distal end with a ring electrode 146 and an extendable helix electrode 148, mounted retractable within an insulating electrode head 144, forming an atrial pace/sense, bipolar electrode pair. Each of the electrodes 146 and 148 are coupled to one of the coiled conductors within the body of the RA/SVC lead 140 and are employed for atrial pacing and for sensing atrial depolarizations or P waves in a manner well known in the art. An elongated, exposed coil atrial defibrillation electrode 142 is also provided, proximal to electrode 146 and coupled to the third conductor within the body of RA/SVC lead 144. Electrode 142 preferably may be about 10.0 cm in length or greater and is configured to extend from the SVC into the RA and toward the tricuspid valve. A bifurcated connector 138 which carries three electrical connectors, each coupled to one of the coiled conductors, is formed at the proximal end of the RA/SVC lead 140 for connection into receptacles of connector block 154.

The CS lead 130 includes a single coiled wire conductor, coupled to an elongated, exposed coil defibrillation electrode 132. CS electrode 132, illustrated in broken outline, is located within the coronary sinus and great vein of the heart 10 and may be about 5.0 cm long. A connector 128 is coupled to the coiled conductor of the CS lead 130 and inserted into a further receptacle of the connector block 154.

The system 150 includes the pulse generator 152 in combination with the leads, with the lead connector assemblies 128, 138, 158 inserted into the connector block 154. The atrial and ventricular leads 130, 140, 160 and the associated pace/sense and cardioversion electrodes may take the form of those corresponding leads disclosed in commonly assigned U.S. Pat. Nos. 5,174,288 to Bardy or 5,165,403 to Mehra.

In addition, the system of electrodes may include a subcutaneous plate defibrillation electrode of the type described in the '288 patent to Bardy. Optionally, insulation of the outward facing portion of the housing of the pulse generator 152 may be provided using a plastic coating, for example parylene or silicone rubber, as is currently employed in some unipolar cardiac pacemakers. However, a portion of the housing may instead be left uninsulated and electrically connected to the defibrillation pulse generator to be used as a subcutaneous cardioversion/defibrillation electrode alone or in combination with one or more of the lead bearing cardioversion/defibrillation electrodes to cardiovert or defibrillate either the atria or ventricles.

It should be noted that the leads and electrode systems as described to this point in regard to FIG. 1 are comprehensive of atrial and ventricular electrode systems and cardioversion/defibrillation pathways that may be combined or separated depending on whether atrial or ventricular cardioversion/defibrillation therapy is undertaken in conjunction with the separate delivery of pacing pulse bursts in accordance with the present invention. As disclosed in U.S. patent application Ser. No. 08/293,769, filed by Min et al on Aug. 19, 1994 for an "Atrial Defibrillator and Method of Use", incorporated in its entirety herein, the addition of the ventricular lead 160 and defibrillation electrode 162 provides a further pathway for atrial defibrillation as well as a ventricular defibrillation pathway. In the former case, atrial cardioversion energy may be delivered between the RA/SVC electrode 142 (alone or optionally coupled with a subcutaneous electrode, e.g. pulse generator housing electrode 156 and the combination of the RV defibrillation electrode 162 and the CS electrode 132. In the latter case, particularly efficient ventricular cardioversion/defibrillation may be effected in a pathway between the RV electrode 162 and a distributed electrode formed by electrically connecting the CS electrode 132 in common with the RA/SVC electrode 23.

The relative current densities in the atria or ventricles during delivery of a defibrillation pulses are defined by the selection and positioning of the atrial defibrillation electrodes and by the three dimensional configurations and relative conductivities of the blood, heart tissue and adjacent body tissue. High current density regions are generally found at the sites of the defibrillation electrodes and low current density regions are generally more remote from the defibrillation electrode sites, with additional variability due to the tissue conductivities and configurations as discussed above. The current densities at various points in the atria can be mapped or simulated using finite element analysis. In the case of the lead system presently considered most practicable for use in treating atrial fibrillation, comprising electrodes located in the right atrium/superior vena cava and coronary sinus as discussed above, one of the lower current density areas is located in the region of the right atrial appendage. In the case of the lead systems presently considered most practicable for use in treating ventricular fibrillation, comprising electrodes located in the right ventricle and in the superior vena cava and/or subcutaneously, as discussed above, one of the lower current density areas is located in the region of the ventricular apex.

As such, the implant sites depicted in FIG. 1 for atrial pace/sense electrode pair 146, 148 and ventricular pace/sense electrode pair 164, 166 fall in low current density regions of the atria and ventricles, respectively, for some known transvenous/subcutaneous electrode combinations depicted, and thus are appropriately placed to practice the present invention.

In another aspect of the present invention, it is noted that following delivery of a defibrillation pulse, tissue in the areas of lower current density may recover from their refractory periods following delivery of a defibrillation pulse quicker than the bulk of the myocardial cells in the heart chamber subjected to the defibrillation pulse. Such an uneven recovery may contribute to unsynchronized depolarizations of cells in the low current density regions, possibly leading to re-fibrillation of the heart chamber. In practice, physicians program a higher defibrillation energy when re-fibrillation is seen or in anticipation of possible re-fibrillation, and the high energy fully saturates all myocardial cells of the heart chamber such that they recover at about the same time. The pulse burst of the present invention may assist in reducing the occurrence of re-fibrillation, without requiring as high a defibrillation pulse energy, due to prolongation of the refractory period of the tissue in the area adjacent the pacing electrodes.

Turning to FIG. 2, it is a functional schematic block diagram of an implantable atrial and/or ventricular pacemaker/cardioverter/defibrillator pulse generator in which the present invention may usefully be practiced. This diagram should be taken as exemplary of the type of pulse generator in which the invention may be embodied, and not as limiting, as it is believed that the invention may usefully be practiced in a wide variety of implementations, including atrial and ventricular only pacemaker/cardioverter/defibrillators which may or may not provide separate programmable anti-tachycardia and bradycardia pacing therapies, programmable cardioversion/defibrillation energies, staged therapies of both, or the like.

With this understanding in mind, the most comprehensive pacemaker/cardioverter/defibrillator pulse generator diagram of FIG. 2 will be described in conjunction with the lead/electrodes of the overall system 150 of FIG. 1. The pulse generator 150 is provided with a terminals schematically identified in FIG. 2 in the receptacles of connector block 154 for making electrical connection with the lead connectors 128, 138 and 158 and is also provided with the electrical terminal or catheter connector output 170 in connector block 154.

With respect to the terminals 310, 311, 318 and 320, terminal 310 is optionally coupled to the un-insulated housing electrode 156. Terminal 320 is attached to RV lead connector 158, and specifically makes connection with the RV defibrillation electrode 162. Terminal 311 is adapted to make electrical connection with RA/SVC cardioversion electrode 142 through lead connector 138 and RA/SVC lead 140. Terminal 318 is adapted to make electrical connection with CS cardioversion electrode 132 through lead connector 128 and CS lead 130.

Terminals 310, 311, 318 and 320 are coupled to high voltage output circuit 234 which includes high voltage switches controlled by cardioversion/defibrillation (CV/DEFIB) control logic 230 via control bus 238. The switches within circuit 234 control which cardioversion electrode sets are employed and which are coupled to the positive and negative terminals of the high voltage output capacitor bank including capacitors 246 and 248 during delivery of the cardioversion shocks.

With respect to the terminals 317, 321, 324 and 326, terminals 324 and 326 are adapted to make electrical connection through connector 158 of RA lead 160 with the ventricular pace/sense electrode pair 164, 166. Terminals 324 and 326 are coupled to the R-wave sense amplifier 200, which preferably takes the form of an automatic gain controlled amplifier providing an adjustable sensing threshold as a function of the measured R-wave amplitude. A V-SENSE signal is generated on R OUT line 202 whenever the signal sensed between electrodes 612 and 614 exceeds the present sensing threshold.

Terminals 317 and 321 are adapted to make electrical connection through connector 138 of RA/SVC lead 140 with the atrial pace/sense electrode pair 146, 148. Terminals 317 and 321 are coupled to the P-wave sense amplifier 204, which preferably also takes the form of an automatic gain controlled amplifier providing an adjustable sensing threshold as a function of the measured P-wave amplitude. An A-SENSE signal is generated on P OUT line 206 whenever the signal sensed between terminals 317 and 321 exceeds the present sensing threshold.

Switch matrix 208 is used to select which of the available terminals are coupled to wide band (0.5–200 Hz) amplifier 210 for use in digital signal analysis. Selection of electrodes is controlled by the microprocessor 224 via data/address bus 218, which selections may be varied as programmed-in through RF transmitter receiver 102 and stored in RAM 226. Signals from the electrodes selected for coupling to bandpass amplifier 210 are provided to multiplexer 220, and thereafter converted to multi-bit digital signals by A/D converter 222, for storage in RAM 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The pacer timing/control circuitry 212 includes programmable digital counters which optionally control the basic time intervals associated with DDD, WI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in RAM 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to terminals 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the RAM 226 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212. Burst or overdrive pacing therapies are delivered through operation of the escape interval counters therein which also define refractory periods during which detection of R-waves and P-waves is ineffective to restart the escape interval counters.

In the event that generation of a cardioversion or defibrillation shock is required, microprocessor 224 employs the escape interval counter to control timing of such cardioversion and defibrillation pulses, as well as associated refractory periods of the sense amplifiers 200, 204. In response to the detection of atrial or ventricular fibrillation or tachyarrhythmia requiring a cardioversion pulse, microprocessor 224 activates CV/DEFIB control logic 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 to the bus 218 and microprocessor 224. When the capacitor voltage reaches a predetermined value set by microprocessor 224, capacitor charging is terminated. Thereafter, timing of the delivery of the cardioversion/defibrillation pulse is controlled by pacer timing/control circuitry 212.

In the context of treating atrial fibrillation, it is desirable to synchronize the delivery of the atrial cardioversion pulse with an R-wave sensed by R-wave sense amplifier 200 in a manner as disclosed in PCT Application No. US92/02829, Publication No. WO 92/18198 by Adams et al, incorporated herein by reference in its entirety. In this reference, careful synchronization of the high voltage atrial defibrillation pulse to the ventricles to avoid inducing of ventricular tachycardia or fibrillation is discussed. Delivery of an atrial defibrillation pulse at an inappropriate time may induce ventricular arrhythmias, including ventricular fibrillation.

In the illustrated comprehensive pulse generator, delivery of the atrial and/or ventricular cardioversion or defibrillation pulses is accomplished by output circuit 234, under control of CV/DEFIB control logic 230 via control bus 238. Output circuit 234 determines whether a monophasic or biphasic pulse is delivered, the polarity of the electrodes, and which electrodes are involved in delivery of the cardioversion pulse. Output circuit 234 also includes high voltage switches which control whether certain of the cardioversion electrodes are coupled together during delivery of the pulse. Alternatively, cardioversion electrodes intended to be coupled together during the pulse may simply be permanently coupled to one another, either exterior to or interior of the pulse generator device housing, and polarity may similarly be pre-set, as in current implantable pacemaker/cardioverter/defibrillator pulse generators. An example of output circuitry for delivery of biphasic pulse regimens to multiple electrode systems may be found in U.S. Pat. Nos. 4,727,877 and 4,953,551 incorporated by reference in their entireties. A specific switching circuit and explanation of the possible electrode combinations and benefits of such combinations is set forth in the above-referenced Minet al application.

Following delivery of the fibrillation or tachycardia therapy the microprocessor 224 then returns the pulse generator operating mode to cardiac pacing and awaits the next successive interrupt due to pacing or the occurrence of a sensed atrial or ventricular depolarization.

For purposes of implementing the present invention, FIGS. 1 and 2 illustrate comprehensively the pulse generator and lead/electrode components that may be selectively employed in one variation to provide atrial cardioversion alone or with ventricular cardioversion back-up if the atrial cardioversion energy induces ventricular fibrillation. In addition, the implementation of the present invention in a variation to provide ventricular only cardioversion/defibrillation therapies is also possible through selective use of the components of the system 150 of FIGS. 1 and 2.

Figure 3:
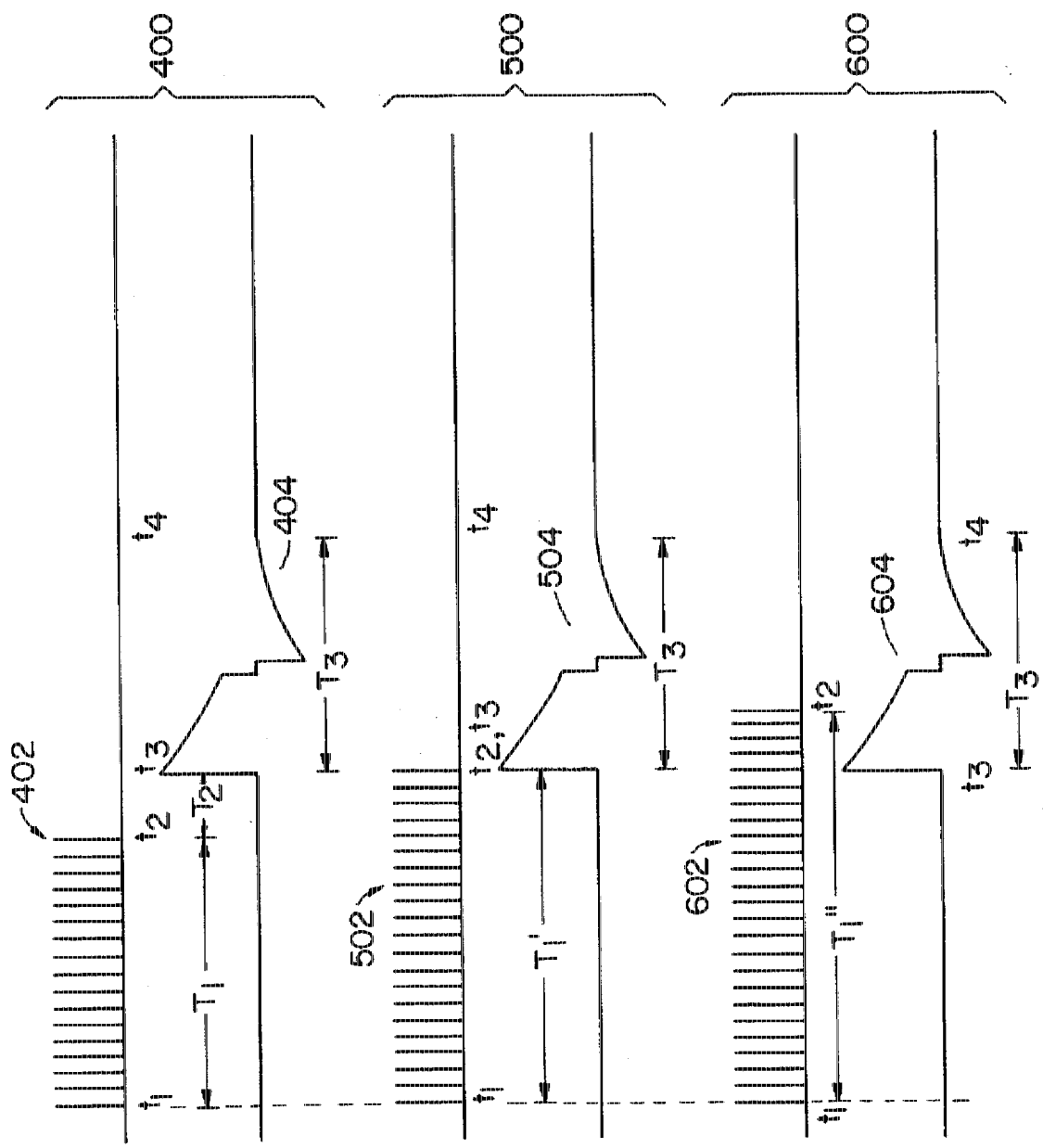
FIG. 3 is a waveform diagram of three defibrillation therapies in accordance with the present invention.

Returning to the cardioversion/defibrillation therapy of the present invention, the pacer timing/control circuitry 212 includes programmable digital counters which optionally control the timing, generation, and delivery of the burst of pacing energy pulses in addition controlling the timing of the delivery of a defibrillation pulse as illustrated in FIG. 3.

The burst pulses may be generated in the same manner as in commercially available implantable neurostimulators, such as employed in the Medtronic® Itrel II nerve stimulator (delivering biphasic pulses). Alternatively, monophasic burst pacing pulse generation circuitry as provided by the Medtronic® Model 2349 Programmable stimulator may be employed. In testing the invention, the inventors employed a Model DTU215 Bloom® stimulator, and a Medtronic® Model 1349 stimulator, both of which produced monophasic pacing pulse bursts, as well as employing a WPI® brand nerve stimulator, which generated biphasic pulse bursts. For purposes of the present invention, any circuit capable of generating pacing energy pulse bursts should be sufficient, but it is believed that monophasic pacing energy pulses of the type illustrated in FIG. 3 are preferably employed. For example, the individual pulses may have a pulse width of about 0.5 ms–1.0 ms and a pulse amplitude of about 5.0 volts, recurring at 20.0 ms or a frequency of 50 Hz.

In the event that atrial or ventricular fibrillation is identified, the typical therapy will be delivery of a high amplitude defibrillation pulse, which may be in excess of 10.0 joules in the case of ventricular fibrillation and may be about 0.50 joule or greater, typically 2 joules or greater, in the case of atrial defibrillation. Lower energy levels will be employed for synchronized cardioversion to convert a high rate tachycardia. As in the case of currently available implantable pacemaker/cardioverter/defibrillator pulse generators, and as discussed in the above-cited references, it is envisioned that the amplitude of the defibrillation pulse may be incremented in response to failure of an initial pulse or pulses to terminate fibrillation.

It is possible that the combined burst pulse/high voltage therapy provided by the present invention will be successful to terminate all atrial fibrillation episodes in any single patient. Unlike ventricular fibrillation, atrial fibrillation is not an immediately life threatening condition. Repeated termination attempts can be undertaken without severe consequences. If the first burst and cardioversion pulse cycle is unsuccessful, multiple cycles may be repeated, with pulse frequency, pulse amplitude, burst duration, burst interval, and/or high energy pulse parameters varied between successive attempts. The pulse frequency may also be varied within a given burst. In particular, pulse burst parameters may be altered by incrementing the pulse frequency within each burst and increasing the duration of each burst. If a sequence of several burst cycles is unsuccessful, the device may disable the burst function for a period of time, e.g. a few hours or more, and renew attempts to terminate fibrillation thereafter. FIG. 3 illustrates the basic timing intervals associated with the delivery of a single pacing energy burst in relation to the delivery of a biphasic cardioversion/defibrillation pulse in first, second and third cardioversion therapies 400, 500, 600 that differ from one another as follows. If the first therapy 400 is directed to treatment of atrial fibrillation, the delivered burst 402 may extend over a programmed burst interval $T_1$ that commences during or before the initiation of charging of the output capacitors 246, 248 at a time $t_1$, chosen such that high voltage capacitor charging should be completed during the burst interval $T_1$, with the burst terminating at time $t_2$. The biphasic defibrillation pulse 404 is delivered at time $t_3$, synchronized to a detected ventricular depolarization, resulting in a variable delay interval $T_2$, determined by the time required to synchronize the delivery of pulse 404.

If the first therapy 400 is directed to treatment of ventricular fibrillation, the delivered burst 402 extends over a programmed burst interval $T_1$ that commences during the charging of the output capacitors 246, 248 at a time $t_1$, chosen such that capacitor charging should be completed during the burst interval $T_1$, with the burst terminating at time $t_2$ as discussed above. Alternatively, the burst interval $T_1$ may be variable commencing at a time $t_1$ chosen such that the expected time to completion of charging is equal to a desired burst interval, with termination of the burst occurring at the time the capacitors are fully charged at time $t_2$. The biphasic defibrillation pulse 404 in either case may be delivered at time $t_3$, following the end of burst interval $T_1$ by a programmed delay interval $T_2$.

The second therapy 500 differs from the first therapy 400 by eliminating the delay interval $T_2$. If the second therapy 500 is directed to treatment of atrial fibrillation, the delivered burst 502 may extend over a variable burst interval $T_1$ that commences during or before the charging of the output capacitors 246, 248 at a time $t_1$, chosen such that capacitor charging should be completed at a time thereafter equal to or somewhat less than the desired burst interval, with the burst actually terminating at time $t_2$, coinciding with delivery of defibrillation pulse 504 following completion of capacitor charging, synchronized to a detected ventricular depolarization.

If the second therapy 500 is directed to treatment of ventricular fibrillation, the delivered burst 502 extends over a programmed burst interval $T_1$ that commences during the charging of the output capacitors 246, 248 at a time $t_1$, chosen such that capacitor charging should be completed during the burst interval $T_1$, with the burst terminating at time $t_2$ as discussed above. Alternatively, the burst interval $T_1$ may be variable commencing at a time $t_1$ chosen such that the expected time to completion of charging is equal to a desired burst interval, with termination of the burst occurring at the time to capacitors are fully charged at time $t_2$. The biphasic defibrillation pulse 504 in either case may be delivered at time $t_2$, coincident with termination of the pulse burst 502.

The third therapy 600 differs from the first therapy 400 by eliminating the delay interval $T_2$ and overlapping the burst interval $T_1$ with the pulse width or duration $T_3$ of the cardioversion pulse 604. If the third therapy 500 is directed to treatment of atrial fibrillation, the delivered burst 602 extends over a variable burst interval $T_1$ that commences during or before the charging of the output capacitors 246, 248 at a time $t_1$, chosen such that capacitor charging should be completed at a time thereafter equal to or somewhat less than the desired burst interval, with the burst actually terminating at time $t_2$, during delivery of defibrillation pulse 604, at a predetermined interval following initiation of defibrillation pulse 604. Pulse 604 is synchronized to a detected ventricular depolarization following completion of capacitor charging.

If the third therapy 600 is directed to treatment of ventricular fibrillation, the delivered burst 602 extends over a programmed burst interval $T_1$ that commences during the charging of the output capacitors 246, 248 at a time $t_1$, chosen such that capacitor charging should be completed during the burst interval $T_1$, with the burst terminating at time $t_2$ as discussed above. Alternatively, the burst interval $T_1$ may be variable commencing at a time $t_1$ chosen such that the expected time to completion of charging is equal to a desired burst interval, with termination of the burst occurring at the time to capacitors are fully charged at time $t_2$. The biphasic defibrillation pulse 604 in either case may be delivered at time $t_3$, a predetermined interval prior to $t_2$.

The three therapies are illustrative of different relationships of the pacing energy burst delivered to the pace/sense electrodes and into the low current density region and the associated high energy pulse delivered to the defibrillation electrodes. Following delivery of the combined therapy, the microprocessor 224 analyzes the electrogram of the heart chamber undergoing the cardioversion therapy to determine whether fibrillation has terminated. If so, any succeeding programmed therapy is canceled. If fibrillation persists, the next scheduled therapy is delivered. Delivery of programmed therapies continues until exhausted. In the context of treatment of atrial fibrillation, if the programmed number of therapies is delivered without termination, therapy is preferably disabled for a period of time, e.g. one hour or more, to prevent excessive battery drain.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A device for providing a combined defibrillation therapy, comprising:
   pacing electrode means for delivering pacing energy pulse bursts to a first chamber of a patient's heart;
   defibrillation electrode means for delivering high energy pulses to said first chamber of said heart;
   means for detecting fibrillation in said first chamber of said heart;
   means for triggering delivery of said combined defibrillation therapy in response to detection of fibrillation in said first chamber of said heart;
   pacing pulse generator means responsive to said triggering means for delivering pacing energy pulse bursts having a frequency of 20 Hz or greater to said pacing electrode means;
   defibrillation pulse generator means responsive to said triggering means for generating said high energy pulses for delivering a high energy pulse to said defibrillation electrode means in conjunction with each delivery of a said pulse burst to said pacing electrode means.

2. The device of claim 1, wherein said triggering means comprises control means for controlling the timing of said pulse bursts and said high energy pulses, said control means comprising:
   means for initiating delivery of said high energy pulses during delivery of said pulse bursts.

3. The device of claim 1, wherein said triggering means comprises control means for controlling the timing of said pulse bursts and said high energy pulses, said control means comprising:
   means for initiating delivery of said high energy pulses on termination of said pulse bursts.

4. The device of claim 1, wherein said triggering means comprises control means for controlling the timing of said pulse bursts and said high energy pulses, said control means comprising:
   means for initiating delivery of said high energy pulses after a delay following termination of said pulse bursts.

5. A device according to claim 2 or claim 3 or claim 4 further comprising means for sensing depolarizations of a second chamber of said heart and wherein said control means comprises means for delivering said high energy pulses synchronized to detected depolarizations of said second chamber of said heart.

6. A device according to claim 2 or claim 3 or claim 4 wherein said pacing pulse generator means comprises means for delivering pacing energy pulse bursts having a frequency of about 50–200 Hz to said pacing electrode means.

7. A method of providing a combined defibrillation therapy, comprising:
   locating a pacing electrode in contact with a first chamber of a patient's heart;
   locating defibrillation electrodes proximate said first chamber of said heart;
   detecting fibrillation in said first chamber of said heart;
   delivering said combined defibrillation therapy in response to detection of fibrillation in said first chamber of said heart, said combined therapy delivering step in turn comprising;
   delivering pacing energy pulse bursts having a frequency of 20 Hz or greater to said pacing electrode and delivering a high energy pulse to said defibrillation electrodes in conjunction with each delivery of said pulse bursts to said pacing electrode.

8. The method of claim 7, wherein said step of delivering said high energy pulses comprises initiating delivery of said high energy pulses during delivery of said pulse bursts.

9. The method of claim 7, wherein said step of delivering said high energy pulses comprises initiating delivery of said high energy pulses on terminations of said pulse bursts.

10. The method of claim 7, wherein said step of delivering said high energy pulses comprises initiating delivery of said high energy pulses after a delay following terminations of said pulse bursts.

11. A method according to claim 8 or claim 9 or claim 10 further comprising sensing depolarizations of a second chamber of said heart and wherein step of delivering said high energy pulses comprises delivering said high energy pulses synchronized to detected depolarizations of said second chamber of said heart, first chamber which is exhibits a relatively lower current density than other portions of said first chamber, during delivery of said high energy pulses.

12. A method according to claim 8 or claim 9 or claim 10 wherein said step of locating said pacing electrode comprises locating said pacing electrode in a region of said first chamber which exhibits a relatively lower current density than other portions of said first chamber, during delivery of said high energy pulses.

13. A method according to claim 8 or claim 9 or claim 10 wherein said step of delivering said pulse bursts comprises delivering pulse bursts having a frequency of 50-200 Hz.

14. A method of providing a combined defibrillation therapy, comprising:

locating defibrillation electrodes proximate said first chamber of said heart;

locating a pacing electrode in contact with a first chamber of a patient's heart;

detecting fibrillation in said first chamber of said heart;

delivering said combined defibrillation therapy in response to detection of fibrillation in said first chamber of said heart, said combined therapy delivering step in turn comprising;

delivering pacing energy pulse bursts to said pacing electrode and delivering a high energy pulse to said defibrillation electrodes in conjunction with each delivery of said pulse bursts to said pacing electrode;

wherein said step of locating said pacing electrode comprises locating said pacing electrode in a region of said first chamber which exhibits a relatively lower current density than other portions of said first chamber, during delivery of said high energy pulses.

15. A method of providing a combined defibrillation therapy, comprising:

locating defibrillation electrodes proximate a first chamber of said heart;

locating a pacing electrode in contact with said first chamber of a patient's heart;

detecting fibrillation in said first chamber of said heart;

sensing depolarizations of a second chamber of said heart;

delivering said combined defibrillation therapy in response to detection of fibrillation in said first chamber of said heart, said combined therapy delivering step in turn comprising;

delivering pacing energy pulse bursts to said pacing electrode and delivering a high energy pulse to said defibrillation electrodes, synchronized to detected depolarizations of said second chamber of said heart in conjunction with delivery of said pulse bursts to said pacing electrode.

16. The method of claim 14 or claim 15, wherein said step of delivering said high energy pulses comprises initiating delivery of said high energy pulses during delivery of said pulse bursts.

17. The method of claim 14 or claim 15, wherein said step of delivering said high energy pulses comprises initiating delivery of said high energy pulses on terminations of said pulse bursts.

18. The method of claim 14 or claim 15, wherein said step of delivering said high energy pulses comprises initiating delivery of said high energy pulses after a delay following terminations of said pulse bursts.

19. A method of providing a combined defibrillation therapy, comprising:

locating defibrillation electrodes proximate a first chamber of said heart;

locating a pacing electrode in contact with a first chamber of a patient's heart;

detecting fibrillation in said first chamber of said heart;

sensing depolarizations of a second chamber of said heart;

delivering said combined defibrillation therapy in response to detection of fibrillation in said first chamber of said heart, said combined therapy delivering step in turn comprising;

delivering pacing energy pulse bursts to said pacing electrode and delivering high energy pulses to said defibrillation electrodes during delivery of said pulse bursts to said pacing electrode.

20. A device for providing a combined defibrillation therapy, comprising:

pacing electrode means for delivering pacing energy pulse bursts to a first chamber of a patient's heart;

defibrillation electrode means for delivering high energy pulses to said first chamber of said heart;

means for detecting fibrillation in said first chamber of said heart;

means for sensing depolarizations of a second chamber of said heart;

means for triggering delivery of said combined defibrillation therapy in response to detection of fibrillation in said first chamber of said heart;

pacing pulse generator means responsive to said triggering means for delivering pacing energy pulse bursts to said pacing electrode means;

defibrillation pulse generator means responsive to said triggering means for generating said high energy pulses for delivering a high energy pulse to said defibrillation electrode means in conjunction with delivery of a said pulse burst to said pacing electrode means, synchronized to a detected depolarization of said second chamber of said heart.

21. The device of claim 20, wherein said triggering means comprises control means for controlling the timing of said pulse bursts and said high energy pulses, said control means comprising:

means for initiating delivery of said high energy pulses during delivery of said pulse bursts.

22. The device of claim 20, wherein said triggering means comprises control means for controlling the timing of said pulse bursts and said high energy pulses, said control means comprising:

means for initiating delivery of said high energy pulses on termination of said pulse bursts.

23. The device of claim 20, wherein said triggering means comprises control means for controlling the timing of said pulse bursts and said high energy pulses, said control means comprising:

means for initiating delivery of said high energy pulses after a delay following termination of said pulse bursts.

24. A device for providing a combined defibrillation therapy, comprising:

pacing electrode means for delivering pacing energy pulse bursts to a first chamber of a patient's heart;

defibrillation electrode means for delivering high energy pulses to said first chamber of said heart;

means for detecting fibrillation in said first chamber of said heart;

means for triggering delivery of said combined defibrillation therapy in response to detection of fibrillation in said first chamber of said heart;

pacing pulse generator means responsive to said triggering means for delivering pacing energy pulse bursts to said pacing electrode means;

defibrillation pulse generator means responsive to said triggering means for generating said high energy pulses for delivering high energy pulses to said defibrillation electrode means during delivery of said pulse bursts to said pacing electrode means.

25. A device for providing a combined defibrillation therapy, comprising:

pacing pulse generator means for generating pacing pulses;

pacing electrode means coupled to said pacing pulse generator means for delivering said pacing pulses to a first chamber of a patient's heart;

defibrillation pulse generator means for generating high energy pulses;

defibrillation electrode coupled to said defibrillation pulse generator means, for delivering said high energy pulses to said first chamber of said heart;

means for activating said pacing pulse generator means to deliver pacing pulses to said first chamber of said heart in an anti-bradycardia pacing mode;

means for detecting fibrillation in said first chamber of said heart;

means for triggering delivery of a combined defibrillation therapy in response to detection of fibrillation in said first chamber of said heart; comprising means for triggering said pacing pulse generator means to deliver a pulse burst to said chamber of said heart and means for triggering said defibrillation pulse generator means to deliver a high energy pulse to said chamber of said heart in conjunction with delivery of said pulse burst to said chamber of said heart.

26. A device for providing a combined pacing and defibrillation therapy, comprising:

pacing pulse generator means for generating pacing pulses;

pacing electrode means coupled to said pacing pulse generator means for delivering said pacing pulses to a first chamber of a patient's heart;

defibrillation pulse generator means for generating high energy pulses, said defibrillation pulse generator comprising a high voltage output capacitor;

defibrillation electrode means coupled to said defibrillation pulse generator means, for delivering said high energy pulses to said first chamber of said heart;

means for detecting fibrillation in said first chamber of said heart;

means for triggering delivery of a combined defibrillation therapy in response to detection of fibrillation in said first chamber of said heart; comprising means for initiating charging of said high voltage output capacitor, means for defining a first time interval which will expire after charging of said high voltage capacitor, means for triggering said pacing pulse generator means to deliver pulse bursts to said chamber of said heart commencing on the beginning of said first time interval and continuing until said high voltage capacitor is charged and means for triggering said defibrillation pulse generator means to deliver high energy pulses to said chamber of said heart means in response to said high voltage capacitor being charged.

27. A device according to claim 26 wherein said means for triggering said pacing pulse generator comprises means for terminating delivery of said pulse bursts on expirations of said first time intervals.

28. A device according to claim 26 wherein said means for triggering said pacing pulse generator comprises means for terminating delivery of said pulse bursts on deliveries of said high energy pulses.

29. A device according to any of claims 24, 25, 26 or 27, further comprising:

means for sensing depolarizations of a second chamber of said heart; and wherein said means for triggering said defibrillation pulse generator means comprises means for triggering said defibrillation pulse generator means to deliver high energy pulses to said chamber of said heart means in response to a sensed depolarization of said second chamber of said heart, after said high voltage capacitor is charged.

30. A method of providing a combined pacing and defibrillation therapy, comprising:

employing a pacing pulse generator to deliver pacing pulses to a first chamber of a heart in an anti-bradycardia pacing mode;

detecting fibrillation in said first chamber of said heart;

delivering a combined defibrillation therapy, in response to detection of fibrillation in said first chamber of said heart, by employing said pacing pulse generator to deliver pulse bursts to said first chamber of said heart and by employing a defibrillation pulse generator means to deliver high energy pulses to said first chamber of said heart means in conjunction with delivery of said pulse bursts to said first chamber of said heart.

31. A method of providing a combined defibrillation therapy, comprising:

detecting fibrillation in a first chamber of said heart;

delivering a combined defibrillation therapy in response to detection of fibrillation in said first chamber of said heart by initiating charging of a high voltage output capacitor and defining a first time interval which will expire after charging of said high voltage capacitor, and delivering a low energy pulse burst to said first chamber of said heart commencing on the beginning of said first time interval and continuing until said high voltage capacitor is charged and discharging said high voltage capacitor to deliver a high energy pulse to said first chamber of said heart means in response to said high voltage capacitor being charged.

32. A method according to claim 31 wherein said pulse burst delivery step comprises terminating delivery of said pulse burst on expiration of said first time interval.

33. A method according to claim 32 wherein said pulse burst delivery step comprises terminating delivery of said pulse burst prior to delivery of said high energy pulse.

34. A method according to any of claims 30, 31, 32 or 33, further comprising:

sensing depolarizations of a second chamber of said heart; and wherein said high energy pulse delivery step comprises delivering said high energy pulse in response to a sensed depolarization of said second chamber of said heart, after said high voltage capacitor is charged.

* * * * *

UNITED STATES PATENT AND TRADEMARK OFFICE
CERTIFICATE OF CORRECTION

PATENT NO. : 5,713,924
DATED : February 3, 1998
INVENTOR(S) : Min, et. al.

It is certified that error appears in the above-identified patent and that said Letters Patent is hereby corrected as shown below:

Col. 14, lines 63, 64, 65:

Beginning in line 63, after "heart." delete "first chamber which is exhibits a relatively lower current density than other portions of said first chamber, during delivery of said high energy pulses."

Signed and Sealed this

Twenty-ninth Day of September, 1998

Attest:

BRUCE LEHMAN

Attesting Officer

Commissioner of Patents and Trademarks